United States Patent [19]

Hogle

[11] Patent Number: 4,881,277
[45] Date of Patent: Nov. 21, 1989

[54] PROTECTIVE GLOVE AND METHOD OF MANUFACTURE

[76] Inventor: Gregory A. Hogle, 1675 Niagara, Denver, Colo. 80220

[21] Appl. No.: 207,262

[22] Filed: Jun. 15, 1988

[51] Int. Cl.⁴ .......................................... A41D 19/00
[52] U.S. Cl. ...................................... 2/169; 2/161 R; 2/168
[58] Field of Search ............... 2/168, 169, 167, 161 R, 2/161 A, 164, 16, 2.5

[56] References Cited

U.S. PATENT DOCUMENTS

| | | | |
|---|---|---|---|
| 532,880 | 1/1895 | Hunicke | 2/164 X |
| 3,564,614 | 2/1971 | Getchell | 2/161 |
| 3,633,216 | 1/1972 | Schonholtz | 2/168 |
| 3,874,000 | 4/1975 | Altman | 2/164 X |
| 3,942,193 | 3/1976 | Pugh | 2/167 |
| 4,197,592 | 4/1980 | Klein | 2/164 X |
| 4,430,759 | 2/1984 | Jackrel | 2/159 |
| 4,520,056 | 5/1985 | Jackrel | 428/68 |
| 4,545,841 | 10/1985 | Jackrel | 156/290 |
| 4,658,444 | 4/1987 | Figlia et al. | 2/168 X |
| 4,662,006 | 5/1987 | Ross, Jr. | 2/158 |
| 4,677,697 | 7/1987 | Hayes | 2/159 |
| 4,679,257 | 7/1987 | Town | 2/164 |
| 4,696,065 | 9/1987 | Elenteny | 2/168 |
| 4,742,578 | 5/1988 | Seid | 2/168 X |
| 4,745,635 | 5/1988 | Kinnear | 2/161 R |
| 4,771,482 | 9/1988 | Shlenker | 2/168 X |

*Primary Examiner*—Peter Nerbun
*Attorney, Agent, or Firm*—Dorr, Carson, Sloan & Peterson

[57] ABSTRACT

A protective glove for protection against infection due to puncture or rupture of the glove during surgery formed from two protective layers. The outer layer is formed with substantially the same finger lengths as the inner layer and slightly larger diametrical width than the inner layer. This forms a protective clearance space while providing tactile sensitivity to allow fine surgical techniques to be performed.

8 Claims, 2 Drawing Sheets

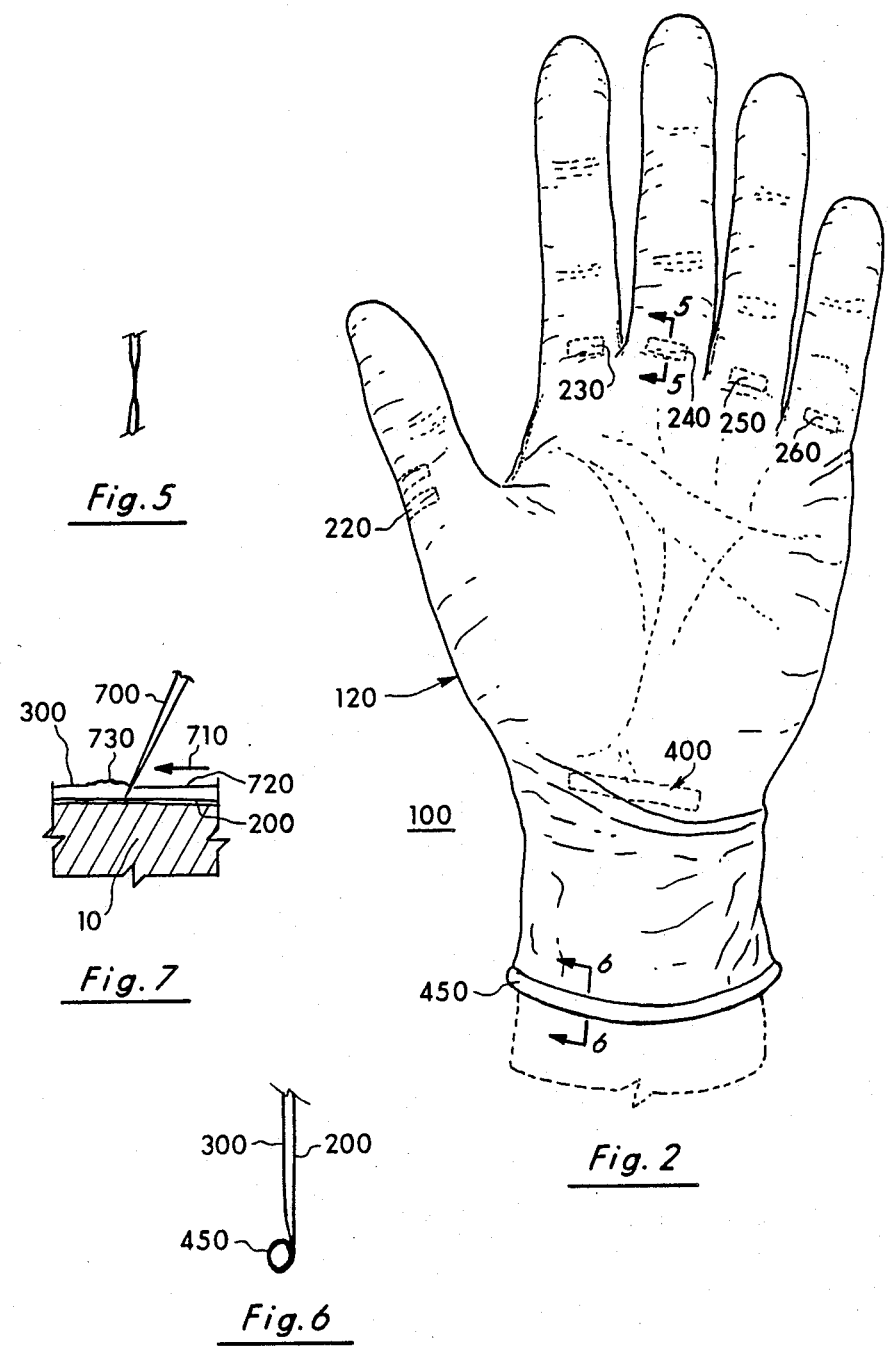

PROTECTIVE GLOVE AND METHOD OF MANUFACTURE

BACKGROUND OF THE INVENTION

1. Field of the Invention

This invention relates to protective gloves of the type used by surgeons and other medical personnel to afford protection from contamination and infection and, in particular, to surgical gloves having multiple layers.

2. Statement of the Problem

Thin latex protective or surgical gloves are presently used by surgeons, nurses and other medical personnel during surgery and other medical procedures. Such gloves are now being used by police, firemen and other emergency personnel.

These gloves provide protection from contamination or infection from the wearer to the patient as well as preventing contamination and the spread of infection from the patient to the wearer. These gloves are susceptible to puncture and rupture during use especially by sharp surgical devices, risking exposure of the surgeon or other wearer as well as the patient to possible infection. In view of the alarming increase of Acquired Immune Deficiency Syndrome (AIDS), this is a matter of great concern to the medical and emergency community.

Currently, to prevent the risk of possible infection should a glove be punctured, many surgeons use a "double-gloving" technique. This technique involves either a correctly sized glove worn over a glove of the next larger size or a larger glove worn under the correctly sized glove. However, there are problems associated with the use of the "doublegloving" technique. If the larger glove is worn over the correctly sized glove, then as excess amount of glove forms at the fingertips. The outer glove further tends to slip and bunch during use over the inner glove. If the larger glove is worn under the correctly sized glove, then a bunching of the excess glove occurs at the finger tips. In both instances, there is a loss of tactile sensitivity; this impedes the performance of fine surgical technique. The use of double gloves also constricts the movement of the hand causing discomfort and tiring of the hand muscles.

Other solutions to the problem of preventing glove puncture include reinforced gloves such as the type disclosed by U.S. Pat. No. 3,633,216. This patent discloses a surgical glove comprising an increased thickness at the thumb and index digit portions of the gloves. The increased thicknesses are formed by dipping the exterior of the digit portions in fluid latex, then curing and vulcanizing the digit portion forming an integral cover part on the glove at high risk areas. In one embodiment, a space is formed between the cover and underlying digit member which is filled with an indicator substance. This type of glove does not provide adequate protection across the palm and back of the hand. These gloves create decreased tactile sensitivity at the precise areas where such sensitivity is needed. The surgeon must also rely on visual sighting of the indicator to know when a puncture of the glove has occurred.

Other types of surgical gloves include multilayer gloves such as disclosed by U.S. Pat. No. 4,696,065. This type of glove comprises a flexible elastic glove having multiple layers wherein each outermost layer is removed after use and discarded. The gloves are formed by dipping a mold into fluid latex to form a layer, curing the layer, spraying a release agent onto the layer and repeating the operation to form additional layers. This type of glove has the same disadvantages as double-gloving and reinforced gloves. There is decreased sensitivity as well as no warning to the wearer that a puncture of the glove has occurred until the wearer's hand is punctured.

There exists a need for an improved surgical glove which will provide protection and warning to the wearer of puncture during use while allowing sufficient tactile sensitivity to perform fine surgical technique. The need also exists for a surgical glove with added protection that will provide ease of hand movement and reduce hand fatigue. These and other features are accomplished by the present invention.

SOLUTION TO THE PROBLEM

The present invention solves these problems with a surgical glove having two layers designed to provide adequate protection from the risk of puncture while allowing the wearer sufficient tactile sensitivity to peform fine surgical techniques.

Another feature of the present invention is a surgical glove which allows advance warning to the wearer that the outer layer has been punctured before the wearer's hand is exposed or punctured.

The present invention also provides a glove that will not constrict the wearer's hand thus increasing freedom of movement and reducing fatique.

The gloves contemplated by the present invention are much quicker to put on than the time taken by the more cumbersome double-gloving technique.

These and other advantages of the present invention will be apparent from the ensuing descriptions and drawings.

SUMMARY OF THE INVENTION

The present invention comprises a surgical glove having a thin latex inner layer correctly sized to fit the wearer's hand. a thin latex outer layer is formed from a mold only slightly larger in diameter than the inner glove. This outer layer is significantly smaller than would be the next larger glove size. The lengths of the digit portions of the outer layer are essentially the same length as the lengths of the digit portions of the inner layer. The diameter of the outer layer is of slightly greater size than the diameter of the inner layer. The layers are bonded together at the base of each digit portion on the palm side, on the lower knuckles on the back of the hand and at the wrist.

The greater diameter of the outer layer across the width of the hand provides a slight clearance space between the layers. Should the outer layer be punctured by a needle, the outer layer will be immediately displaced passively by the needle along the plane of the layer. The outer layer will bunch on one side of the needle and stretch on the outer side of the needle. The bunching of the outer layer material will increase the resistance to further penetration of the needle. Also, the movement of the outer layer will alter the angle of attach of the needle, thereby reducing the ability of the needle to puncture the inner layer. The movement of the outer layer will also be noticeable by the wearer and allow reflex time for the wearer to react and further limit the possiblity of penetration of the inner layer of the glove.

The inner layer is able to move the stretch at key areas inside the outer layer, i.e. at the back of the hand and at finger areas across the knuckles thus allowing free movement of the wearer's hand without constriction. The outer layer is prevented from slipping or bunching during use by bonding the layers together at a limited number of strategic areas. This combination of layers provides freedom of movement of the wearer's hand, tactile sensitivity at the wearer's finger tips and protection from puncture during use.

The ends of the two layers are rolled and bonded together beyond the wrist area to form a convenient gripping means to prevent the separation of the layers when the glove is pulled on.

Other features and advantages of the present invention will become apparent from the following detailed description of one embodiment, present in conjunction with the accompanying drawings.

BRIEF DESCRIPTION OF THE DRAWING

FIG. 2 is an outline view of the palm side of the gloves of the present invention;

FIGS. 4–6 are partial cross-sections of the glove of FIGS. 1 and 2 showing the bonding of the two layers together; and FIG. 7 illustrates the puncturing of the outer layer of the glove of the present invention by a sharp instrument.

DETAILED DESCRIPTION OF THE INVENTION

Figure 1:
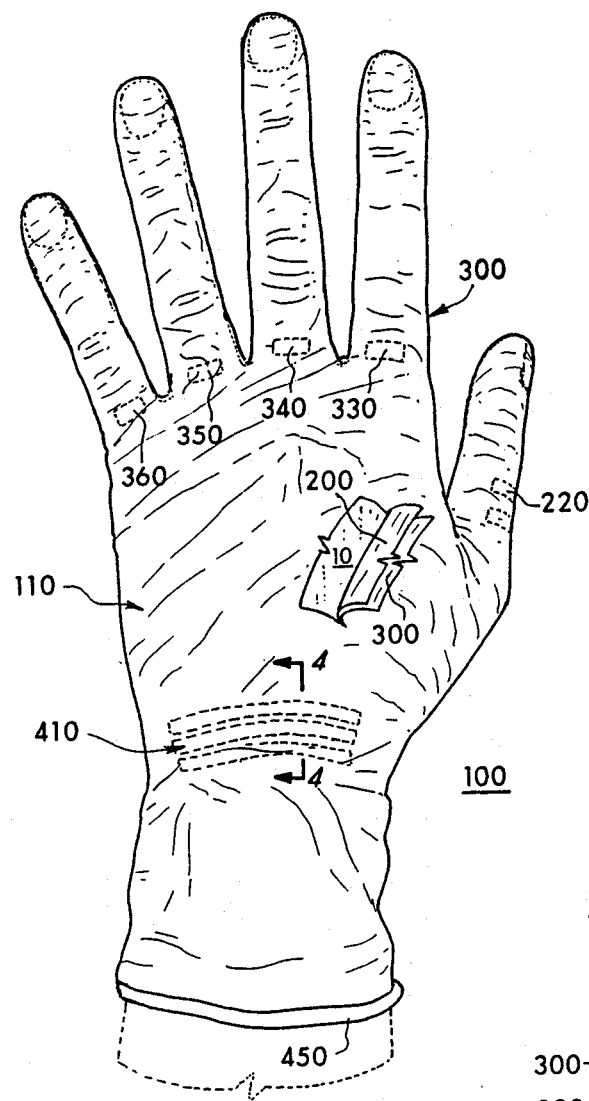
FIG. 1 is an outline view of the back side of the gloves of the present invention.
Figure 4:
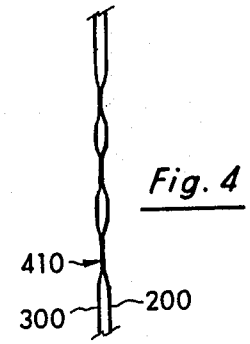
Figure 3:
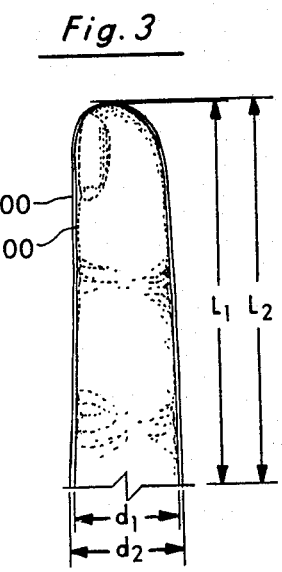
FIG. 3 is a cross-sectional view of a digit portion of the present invention.

A preferred embodiment of the present invention is illustrated in FIG. 1. The surgical glove 100 of the present invention comprises an inner layer 200 and an outer layer 300. The construction of the inner layer 200 is similar to a conventional surgical glove typically formed of thin latex rubber. This layer is designed to fit closely and tightly over the wearer's hand 10 to pemit maximum sensitivity and manual dexterity while protecting against contamination of infection. The outer layer 300 is formed from a mold (not shown) only slightly larger in diameter than the inner layer 200. The inner and outer layer finger lengths L1 and L2 respectively as shown in FIG. 3 are substantially the same length while the diameter d2 of the outer layer is slightly larger than the diameter d1 of the inner layer as shown in FIG. 3. The difference between d1 and d2 is larger than the difference between L1 and L2. For example, in the preferred embodiment, the ratio of L2/L1 is 1.005 and the ratio of d2/d1 is 1.1. This is a generalized ratio and may vary, depending on the overall glove size.

Having substantially the same length (i.e., within 0.5 to 1.0 percent) at the digit portions provides the desired tactile sensitivity at the fingertips to allow fine surgical technique to be performed. The larger diameter d2 of the outer glove (i.e., about 10 percent) to the inner diameter d1 across the width of the hand creates a clearance space between the layers. This clearance space provides a margin of safety from puncture of the wearer's hand for two reasons. First, should the outer layer be punctured, the needle or other device will passively displace the outer layer thereby altering the angle of the needle or other instrument to move along the surface of the inner layer 200 as shown in FIG. 7. In FIG. 7, a sharp object such as a needle 700 has pierced the outer layer 300 and is moving in direction of arrow 710. This causes stretching of the outer layer in region 720 and bunching in region 730 thus increasing the resistance to further penetration of the needle as well as changing the angle of penetration of the needle. Secondly, the movement of the outer layer will immediately warn the wearer of the puncture thereby allowing reflex time for the wearer to react and further limit the possibility of penetration of the inner glove layer.

The inner and outer layers are secured by bonding at certain areas on the glove. These areas include the base of each digit portion as shown in FIG. 2 at 220, 230, 240, 250 and 260 and on the wrist at 400 on the palm side and as shown in Figure 1 at the lower knuckles 220, 330, 340, 350 and 360 and on the wrist at 410 on the back side.

The bonding at the selected points allows the glove to freely flex at areas where the hand flexes, i.e. across the knuckles, at the back of the hand and at the wrist without the outer layer constantly slipping and pulling. This greatly reduces the fatique of the hand muscles which normally are pulling against the constraints of a separate outer glove. The hand is able to more freely move, thus providing greater flexibility in the performance of medical procedures.

The bonding is typically by heat treatment but could easily be by other known processes such as: adhesives, cements, clips, or double-sided adhesive strips placed between the inner and outer glove. The ends of the layers beyond the wrist at 450 are rolled together and bonded as shown in FIGS. 1 and 2. This bonding could also be performed by heat treatment, cement, adhesive, or clip. This allows a convenient way of pulling the gloves on without separating the layers.

The description of the preferred embodiment is not meant to strictly limit the invention to the above description and numerous modifications or alterations may be made within the scope and range of the inventive concept.

In use, the surgeon or other medical personnel selects the correct glove size. The gloves are quickly and easily pulled on over the wearer's hands in the same manner as a conventional signal surgical glove. The slightly larger diameter d2 of the outer layer 300 forms a protective clearance space 290 between the two glove layers, not only at the fingers which are typically the high risk areas for punctures or ruptures but also across the palms and the back of the hands. Should the outer layer 300 be punctured or ruptured during use by a needle or other surgical instrument, the outer layer is passively displaced by the instrument as shown in FIG. 7. This will deflect the instrument from further puncturing the inner layer 200 as well as increasing the resistance to further penetration by the needle. The movement of the outer layer 300 will also serve to warn the wearer and allow reflex time for the wearer to react and further limit the possibility of the wearer's hand being punctured.

The glove 100 is particularly designed not only to provide protection from infection by puncture of the glove but to also provide a surgical glove that will allow the wearer sufficient tactile sensitivity and freedom of hand movement in order to perform fine surgical techniques. The substantially same length of the digit portions of the outer and inner layers allows the wearer to have markedly more sensitivity than the "double-gloving" or the multilayered gloves of the prior art.

The bonding of the layers only at strategic points allows ease of hand flexing and movement without the outer layer 300 slipping or bunching relative to the inner layer 200. This greatly reduces the discomfort of wearing double gloves or the multi-layered gloves as well as reducing hand fatigue of the wearer.

If desired, a third layer can be easily added in much the same way as the second layer. The third layer will povide even greater protection from an accidental puncture or rupture during use. The relative thicknesses of the inner and outer layers may also be varied to provide differing degrees of protection. It is also contemplated to use different materials in either or both of the glove layers and that substances could be added in the area between the layers.

The gloves are easily manufactured. The inner layer 200 is formed of thin latex, such as typical surgical glove. This layer is selected to be correctly sized to a wearer's hand. The outer layer 300 is also formed of thin latex from a mold (not shown) only slightly larger in diameter than the inner layer 200. The lengths of the digit portions of the outer layer 300 are substantially the same length of the digit portions of the inner layer 200. The inner and outer layers are bonded together at selected points, such as at the base of the digit portions 220-260 on the palm side of the glove, at the knuckles of the digit portions 330-360 on the back side of the glove and on the wrist 400, 410 on both sides of the glove. The ends of the inner and outer layers extending beyond the wrist are bonded and rolled together to form a convenient gripping means 450.

The present invention is not meant to be limited to the above decription of the preferred embodiment but also encompasses all other modifications and alterations within the spirit and scope of the inventive concept.

I claim:

1. A glove for protection against puncture, said glove comprises a first inner layer and a separate second outer layer, said outer layer comprising a slightly wider diametrical dimension than said inner layer thereby forming a clearance space between said layers and means to allow said glove to freely flex at areas where the user's hand normally flexes without said outer layer slipping or pulling relative to said inner layer while maintaining said clearance space, said glove means comprising means to secure the inner layer and outer layer together at only selected points; and. selected points comprise attachment areas at the base of the digit portions of said glove, on the palm side of said glove, at the knuckles of said digit portions on the back side of said glove and on the wrist area on said palm and back sides of said glove.

2. A glove for protection against puncture, said glove comprises a first inner layer and a separate second outer layer, said outer layer comprising a slightly wider diametrical dimension than said inner layer thereby forming a clearance space between said layers and means to secure the inner layer and outer layer together, wherein said glove further comprises a wrist portion extending beyond the wearer's wrist, said wrist portion comprising said inner layer and said outer layer rolled together and bonded at their ends to form a gripping means to enable said gloves to be pulled onto said wearer's hands without separating said layers.

3. A glove for protection against punctures, having a plurality of digit member portions, said glove comprises a first inner layer and a separate outer layer, said outer layer comprising a slightly larger diametrical dimension than said inner layer thereby forming a protective clearance space between said layers, and the length of said outer layer digit member portions being substantially the same length as the length of said inner layer digit member portions, wherein said glove further comprises means to allow said glove to freely flex at areas where the user's hand normally flexes without said outer layer slipping or pulling relative to said inner layer while maintaining said clearance space, said glove means comprising means to secure said inner layer and said outer layer together at only selected points, said selected points comprise bonding areas at the base of said digit portions on the palm side of said glove, at the knuckles of said portions on the back side of said glove and on the wrist area on said palm and back sides of said glove.

4. A glove for protection against punctures, having a plurality of digit member portions, said glove comprises a first inner layer and a separate outer layer, said outer layer comprising a slightly larger diametrical dimension than said inner layer thereby forming a protective clearance space between said layers, and the length of said outer layer digit member portions being substantially the same length as the length of said inner layer digit member portions, wherein said glove further comprises a wrist portion extending beyond the wearer's wrist, said wrist portion comprises said inner layer and outer layer rolled together and bonded at their ends to form a gripping means to enable said glove to be pulled onto said wearer's hands without separating said layers.

5. A glove for protection against punctures, said glove comprises a first inner layer and a separate second outer layer, and means to allow said glove to freely flex at areas where the wearer's hand normally flexes without said outer layer slipping or pulling relative to said inner layer, said glove means comprises means to secure said inner and outer layers together at only selected points to allow said freedom of movement of said glove-wearer's hand, wherein said selected points comprise bonding areas at the base of the digit portions of said glove on the palm side of said glove, at the knuckles of said digit portions on the back side of said glove and on the wrist area on said palm and back sides of said glove.

6. A glove for protection against punctures, said glove comprises a first inner layer and a separate second outer layer, and means to secure said inner and outer layers together at selected points to allow freedom of movement of the glove-wearer's hand, wherein said glove further comprises a wrist portion extending beyond the wearer's wrist, said wrist portion comprising said inner layer and outer layer rolled together and bonded at their ends to form a gripping means to enable said glove to be pulled onto said wearer's hands without separating said layers.

7. A glove for protection against puncture, said glove comprises a first inner layer, a separate second outer layer, means to bond said layers together at selected points and a wrist portion; said outer layer comprises a larger diametrical dimension of about ten percent than said inner layer thereby forming a protective clearance space between said layers, said outer layer further comprises digit member portions having lengths that are less than one percent different from the lengths of the digit member portions of said inner layer; said selected points comprise the base of said digit portions on the palm side of said layers, the knuckles of said digit portions on the back side of said layers and on the wrist area on said palm and back sides of said layers; and said wrist portion comprises said inner and outer layers bonded and rolled together at their ends extending beyond the wearer's wrist to form a gripping means.

8. A method of forming surgical gloves for protection against punctures, said method comprises the steps of:
   (a) forming a first inner layer;
   (b) forming a separate second outer layer of slightly larger diametrical width and of substantially same finger lengths as the first inner layer;
   (c) bonding said inner and outer layers at bonding areas at the base of the digit member portions on the palm side of said glove, at the knuckles of said digit portions on the back side of said glove and on the wrist portion on said palm and back sides of said glove to allow flexibility of hand movement;
   (d) rolling the ends of said inner and outer layers extending beyond the wrist portions together to form gripping means.

* * * * *